United States Patent [19]

McBride, Jr. et al.

[11] Patent Number: 5,744,682

[45] Date of Patent: Apr. 28, 1998

[54] ALKYLATION PROCESS USING A CATALYST WITH NON-UNIFORM METAL DISPERSION

[75] Inventors: Thomas K. McBride, Jr., Arlington Heights; Maureen L. Bricker, Buffalo Grove; Karl Z. Steigleder, Glen Ellyn, all of Ill.

[73] Assignee: UOP, Des Plaines, Ill.

[21] Appl. No.: 454,479

[22] Filed: May 30, 1995

Related U.S. Application Data

[62] Division of Ser. No. 270,291, Jul. 5, 1994, abandoned.

[51] Int. Cl.⁶ .............................. C07C 2/58; C07C 2/56; B01J 23/58
[52] U.S. Cl. .................. 585/728; 585/709; 585/721; 585/722; 585/726; 585/727; 502/327; 502/328
[58] Field of Search .................... 585/722, 726, 585/727, 728, 709; 502/327, 328, 721

[56] References Cited

U.S. PATENT DOCUMENTS

| | | | |
|---|---|---|---|
| 2,620,314 | 12/1952 | Hoeckstra | 252/448 |
| 2,999,074 | 9/1961 | Bloch et al. | 252/442 |
| 5,012,027 | 4/1991 | Abrevaya et al. | 502/327 |
| 5,017,541 | 5/1991 | Schmidt et al. | 502/169 |

OTHER PUBLICATIONS

B. R. Shah in "Handbook of Petroleum Refining Processes", R. A. Meyers, editor, McGraw-Hill Book Company, 1986, pp. 1–3 through 1–28 (no month avail.).

*Primary Examiner*—Glenn Caldarola
*Assistant Examiner*—In Suk Bullock
*Attorney, Agent, or Firm*—Thomas K. McBride; Eugene I. Snyder; Frank S. Molinaro

[57] ABSTRACT

A novel catalyst for alkylating an alkene with an alkane to give an alkylate product has been developed. The catalyst comprises a refractory inorganic oxide on which is dispersed a Group VIII metal, a metal cation and the reaction product of a metal halide and bound surface hydroxyl groups of the refractory inorganic oxide. The catalyst is characterized in that the Group VIII metal is concentrated in an outer layer of the catalyst particle.

11 Claims, No Drawings

ALKYLATION PROCESS USING A CATALYST WITH NON-UNIFORM METAL DISPERSION

This is a divisional of application Ser. No. 08/270,291 filed on Jul. 5, 1994, now abandoned.

FIELD OF THE INVENTION

This invention relates to a novel catalyst. In particular it relates to a catalyst for alkylating an alkene with an alkane to give an alkylate product. The catalyst comprises a particulate refractory inorganic oxide having dispersed thereon at least one Group VIII metal, a metal cation and a third component which is the reaction product of a metal halide and bound surface hydroxyl groups of the refractory inorganic oxide. The catalyst is characterized in that the Group VIII metal is concentrated in an outer layer of the catalyst particle.

BACKGROUND OF THE INVENTION

In the oil industry the term "alkylate" generally refers to the product of the alkylation of $C_2$–$C_6$ olefins with $C_4$–$C_6$ alkanes (generally known as motor fuel alkylation). The product is a mixture of alkanes. The main use of alkylate is as a component in motor fuel and thus, it is desirable that the alkylate contain branched paraffins and especially trimethylpentanes, since these paraffins have a high octane number. Although alkylate was an important component when anti-knock additives were used, its importance has increased significantly owing to the phaseout of lead in gasoline. Finally, increased demand of alkylate is owing to the decreased use of butane because butane evaporates readily, especially in warm weather, contributing to smog formation.

The alkylation of $C_2$–$C_6$ olefins is generally catalyzed by strong acids such as sulfuric and liquid hydrogen fluoride. Commercially, HF has been favored at least in part because of the relative ease of HF regeneration. An overview of HF-catalyzed alkylation is presented by B. R. Shah in "Handbook of Petroleum Refining Processes", R. A. Meyers, editor, McGraw-Hill Book Company, 1986, pp 1–3 through 1–28. Briefly, the HF-catalyzed alkylation process is carried out as follows. Generally, olefinic and isobutane feedstocks are combined and mixed with HF in an alkylation reaction zone. The reactor effluent is separated into the desired alkylate, acid, and other light gases which are predominantly unreacted isobutanes. The HF is either recycled to the reactor directly or regenerated in whole or in part prior to its being recycled to the reactor. Unreacted isobutane is also recycled to the reactor and the alkylate is blended in with the motor fuel pool.

However, recently there has been heavy environmental pressure to eliminate the use of HF as a catalyst. HF (hydrofluoric acid) is classified as an acutely hazardous material and in Southern California the Board of the South Coast Air Quality Management District has required that the use of HF in alkylation be phased out by Jan. 1, 1998. Accordingly, there is a strong need to find a catalyst which can replace HF as an alkylation catalyst. It is also desirable to have a solid acid as the catalyst since this would allow the use of a fixed bed system which is generally preferred over a liquid/liquid system by the petroleum refining industry.

Although solid acid catalysts are known in the art, they have serious drawbacks which have precluded them from being used commercially for the alkylation of $C_2$–$C_6$ olefins. For example, U.S. Pat. No. 2,999,074 discloses an alkylation catalyst comprising a refractory inorganic oxide support having dispersed thereon platinum and the reaction products between one or more of the metal halides (those that are active as Friedel-Crafts catalysts) and the refractory inorganic oxide support, e.g., alumina. The platinum metal provides hydrogenation activity for the olefins. One disadvantage of this type of catalyst is that it is too acidic, which results in the catalyst not only catalyzing the alkylation of the olefins but concurrently cracking some of the various alkylate products. Another disadvantage of these types of catalyst is that they are insufficiently selective, again probably arising from its "excess" acidity. By selectivity is meant the extent of monoalkylation versus multiplealkylation. For example, it is most desirable that the olefin react only with the alkanes initially in the feedstocks. However, in practice some of the alkylation products formed also subsequently react with the olefin in the feedstock to form secondary alkylation products. For example, if the feedstock contains only butanes and butenes, the primary alkylation product would be a $C_8$ paraffin, while secondary alkylation products would be $C_{12}$, $C_{16}$, and so on. Since this type of catalyst has cracking activity, the secondary alkylation products can be cracked to lower molecular weight hydrocarbons. Finally, another side reaction which should be avoided is oligomerization which leads to inefficient olefin consumption.

Applicants have discovered a novel solid alkylation catalyst which has improved selectivity and a much longer life than previously known catalysts. The catalyst of the present invention comprises a particulate refractory inorganic oxide support having dispersed thereon at least one Group VIII metal such as platinum, a metal cation such as potassium and the reaction product of a metal halide, e.g., aluminum chloride, and bound surface hydroxyl groups on said refractory inorganic oxide. The catalyst is characterized in that at least 40 percent of the Group VIII metal present on the catalyst is located within a 100–300 micrometer external layer of the catalyst particle, while the metal cation is uniformly distributed throughout the particle. The increased life of the instant catalyst makes the use of a solid bed alkylation catalyst commercially feasible.

It should be pointed out that U.S. Pat. No. 5,017,541 discloses a catalyst which is used for isomerization and which is composed of a support, a Friedel-Crafts metal halide and a surface layer platinum group metal. However, this reference does not mention alkylation, nor the use of a metal cation such as potassium.

SUMMARY OF THE INVENTION

As stated, this invention relates to a novel catalyst for the alkylation of alkenes with alkanes. Accordingly, one embodiment of the invention is a catalyst comprising a particulate refractory inorganic oxide support having dispersed thereon a first component which is at least one Group VIII metal, a second component which is a metal cation and a third component which is the reaction product of a metal halide and bound surface hydroxyl groups on said refractory inorganic oxide; the catalyst characterized in that at least 40 percent of the first component present on the catalyst is located within a band of about 100 to about 300 micrometers beginning at the surface and extending toward the center of the catalyst particle and the second component is uniformly distributed throughout the particle.

Another embodiment of the invention is a process for alkylating a $C_2$–$C_6$ alkene with a $C_4$–$C_6$ alkane to form an alkylate comprising reacting in the liquid phase the alkene with the alkane under alkylation conditions in the presence of a catalyst comprising a particulate refractory inorganic oxide support having dispersed thereon a first component which is at least one Group VIII metal, a second component which is a metal cation and a third component which is the reaction product of a metal halide and bound surface hydroxyl groups of said refractory inorganic oxide; the catalyst characterized in that at least 40 percent of the first component present on the catalyst is located within a band of about 100 to about 300 micrometers beginning at the surface and extending toward the center of the catalyst particle and the second component is uniformly distributed throughout the particle.

These and other objects and embodiments of this invention will become apparent in the following detailed description.

DETAILED DESCRIPTION OF THE INVENTION

As stated, the instant invention relates to a catalyst for alkylating alkenes with alkanes to give an alkylate which has a high octane number and which can be used in gasoline. This type of alkylation is usually referred to in the art as motor fuel alkylation. One necessary component of these catalysts of the present invention is a particulate refractory inorganic oxide support. Illustrative of the refractory inorganic oxides which can be used are alumina, titania, zirconia, chromia, silica, boria, silica-alumina, aluminum phosphate and mixtures thereof. Of these oxides, alumina is particularly preferred. Included among the phases of alumina which can be used are gamma, delta, eta and theta alumina. It is also required that the refractory inorganic oxide support have a surface area of at least 35 m$^2$/g, preferably greater than 50 m$^2$/g, and most preferably greater than 100 m$^2$/g.

It is also necessary that the refractory inorganic oxide support have bound surface hyroxyl groups by which is meant not adsorbed water but rather hydroxyl (OH) groups whose oxygen atom is bound to the metal of the inorganic oxide support. These hydroxyl groups are sometimes referred to as chemically combined hydroxyl. Since the presence of adsorbed water is generally detrimental to the preparation of the catalyst of this invention, the refractory inorganic oxide supports are first calcined at a temperature sufficient to remove adsorbed water without affecting the hydroxyl groups. Usually, the refractory inorganic oxide support is calcined at a temperature of about 350° C. to about 700° C. for a period of about 1 to about 8 hours. Regardless of the inorganic oxide used as the support, the support can be formed in any desired particulate shape such as spheres, pills, cakes, extrudates, granules, etc. and they may be utilized in any particular size. A preferred shape is spherical with a preferred particle size of about 1.59 millimeters in diameter, though particles as small as 0.79 millimeters and smaller may also be utilized.

One way of preparing a spherical alumina support is by the well known oil drop method which is described in U.S. Pat. No. 2,620,314 which is incorporated by reference. The oil drop method comprises forming an aluminum hydrosol by any of the techniques taught in the art and preferably by reacting aluminum metal with hydrochloric acid; combining the hydrosol with a suitable gelling agent; and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging and drying treatments in oil and ammoniacal solutions to further improve their physical characteristics. The resulting aged gel spheres are then washed and dried at a relatively low temperature of about 80° C. to about 150° C. then calcined at a temperature of about 455° C. to 705° C. for a period of about 1 to about 20 hours. This treatment effects conversion of the hydrogel to the corresponding crystalline gamma-alumina. If theta-alumina is desired then the hydrogel spheres are calcined at a temperature of about 950° C. to about 1,200° C.

Regardless of the refractory inorganic oxide support used, said support has dispersed thereon a first component which is at least one Group VIII metal. The Group VIII metals are iron, cobalt, nickel, ruthenium, rhodium, palladium, osmium, iridium and platinum. Of these nickel, ruthenium, rhodium, palladium, platinum, osmium, iridium are preferred with platinum and palladium especially preferred. A second component which is also dispersed on the support is a metal cation selected from the group consisting of alkali metals, alkaline earth metals, silver and copper(I). The alkali and alkaline earth metals include lithium, sodium potassium, cesium, rubidium, beryllium, magnesium, calcium, strontium, and barium. The amount of the first component which is deposited on the support can vary from about 0.01 to about 2 wt. % and preferably from about 0.1 to about 0.7 wt. %. Similarly, the amount of the second component dispersed on the support can vary from about 0.1 to about 10 wt. % and preferably from about 1 to about 5 wt. %.

The desired Group VIII metal or metals and the second component are dispersed onto the support by the following procedure. First, an aqueous solution of a chelating ligand and at least one metal promoter salt is prepared. The chelating ligands which can be used in the process of this invention include amino acids which upon decomposing do not leave detrimental components on the support, e.g., sulfur. Specific examples of these amino acids include ethylenediaminetetraacetic acid (EDTA), nitrilotriacetic acid, N-methylamninodiacetic acid, iminodiacetic acid, glycine, alanine, sarcosine, α-aminoiso-butyric acid, N,N-dimethylglycine, α, β-diaminopropionate, aspartate, glutamate, histidine, and methionine.

Another necessary component of this first solution is a salt of a metal cation. Examples of the salts of these cation metals which can be used include potassium hydroxide, lithium hydroxide, sodium hydroxide, cesium hydroxide, magnesium hydroxide, etc. The resultant solution is heated to a temperature from about 80° to its boiling point and preferably from 90° C. to about 102° C. The ratio of chelating ligand to the metal salt will vary from about 1 to about 8 and preferably from about 1.5 to about 4.

This first solution is now mixed with a second aqueous solution containing at least one Group VIII metal compound. Of the Group VIII metals which can be dispersed on the desired support, preferred metals are rhodium, palladium, platinum, and nickel with palladium and platinum more preferred and platinum being most preferred. Illustrative of the Group VIII metal compounds which can be used in the process of this invention are chloroplatinic acid, palladic acid, tetraamine platinum chloride, tetraamine palladium chloride, bromoplatinic acid, rhodium chloride, ruthenium chloride, gallium nitrate, nickel chloride, nickel nitrate, cobalt nitrate, iron nitrate and iron chloride.

Mixing of the first and second solutions results in the formation of a complex between the Group VIII metal and the chelating ligand. The metal promoter may also be part of the complex. In order to form the complex, the ratio of chelating ligand to Group VIII metal varies from about 0.5 to about 30 and preferably from about 5 to about 13. The ratio depends on the concentration of promoter metal and Group VIII metal, with higher ratios desirable for higher concentrations of metals. The concentration of the Group VIII metal and promoter metal can vary considerably, but is usually chosen to give a concentration on the support in terms of weight percent of the support (as the metal) from about 0.2 to about 1 wt. % and from about 0.5 to about 3 wt. %, respectively.

The first solution described above may also contain a basic compound selected from the group consisting of ammonium hydroxide and quaternary ammonium compounds having the formula $NR_1R_2R_3R_4{}^+X^-$ where $R_1$, $R_2$, $R_3$, $R_4$ are each methyl, ethyl, propyl, butyl or t-butyl and $X$ is hydroxide. The purpose of adding one or more of these basic compounds is to adjust the pH of the solution in order to vary the distribution of the metals. That is, in some cases it may be desirable to have a uniform distribution of the metals whereas in other cases a greater concentration on the surface may be desirable. Further, the distribution of the Group VIII metal may be different from the distribution of the promoter metal.

Without wishing to be bound by any one theory, it appears that there is a relationship between the isoelectric point (IEP) of the support and the pH of the impregnating solution. Thus, if the IEP is high, say 8, and the pH is low (1–2), then strong bonding or chemisorption may result in surface impregnation of the metal. By increasing the pH to 6–9, a substantially uniform distribution will be obtained. Similarly if both the IEP and pH are low then uniform distribution of the metals will result.

After obtaining the mixed solution, it is aged for a time of about 5 minutes to about 4 hours at a temperature of about 40° C. to about 100° C. The aged mixed solution is now used to deposit the metals onto the support by means well known in the art. Examples of said means include spray impregnation and evaporative impregnation. Spray impregnation involves taking a small volume of the mixed solution and spraying it over the support while the support is moving. When the spraying is over, the wetted support can be transferred to other apparatus for drying or finishing steps.

One particular method of evaporative impregnation involves the use of a steam-jacketed rotary dryer. In this method the support is immersed in the impregnating solution which has been placed in the dryer and the support is tumbled by the rotating motion of the dryer. Evaporation of the solution in contact with the tumbling support is expedited by applying steam to the dryer jacket. The impregnated support is then dried at a temperature of about 60° C. to about 300° C. and then calcined at a temperature of about 300° C. to about 850° C. for a time of about 30 minutes to about 8 hours to give the calcined catalyst. Finally, the calcined catalyst is reduced by heating the catalyst under a reducing atmosphere, preferably dry hydrogen, at a temperature of about 300° C. to about 850° C. for a time of about 30 minutes to about 8 hours. This ensures that the Group VIII metal is in the metallic or zerovalent state.

The resultant catalyst is characterized in that the Group VIII metal is not evenly distributed throughout the support but instead is concentrated toward the surface of the particulate support. That is, at least 40% of the total Group VIII metal is concentrated in a band of about 100 to about 300 micrometers beginning at the surface and extending toward the center of the support. Preferably the metal is concentrated in a band of about 100 to about 200 micrometers beginning at the surface of the particle. Most preferably the band will contain at least 60% of the total concentration of the metal.

An optional step in this process involves oxychlorination of the reduced catalyst described above. If such a step is desired, the catalyst is placed in a reactor and a gaseous stream containing chloride or chlorine is flowed over the catalyst at a flow rate of about 2 lb/hr to about 40 lb/hr, at a temperature of about 300° C. to about 850° C. for a time of about 10 minutes to about 6 hours. The gaseous stream can be a hydrogen chloride/chlorine stream, a water/HCl stream, a water/$Cl_2$ stream or a chlorine stream. The purpose of this step is to provide optimum dispersion of the Group VIII and provide a certain amount of chloride on the final catalyst.

Next, the bound surface hydroxyl groups of the refractory inorganic oxide are reacted with a metal halide having Friedel-Crafts activity. Among the metals which may be used are aluminum, zirconium, tin, tantalum, titanium, gallium, antimony and boron. Suitable halides are the fluorides, chlorides and bromides. Illustrative examples of the metal halides include aluminum chloride, aluminum bromide, zirconium chloride, zirconium bromide, boron trifluoride, titanium tetrachloride, gallium chloride, tin tetrachloride, antimony chloride, tantalum chloride, tantalum fluoride, etc. Of these metal halides the aluminum halides are preferred and especially preferred is aluminum chloride. Except for boron trifluoride, the chlorides are generally the preferred halides.

The reaction between metal halides and the bound surface hydroxyl groups of the inorganic oxide support is carried out by means known in the art such as sublimation or distillation of the metal halide onto the surface of the particles of the inorganic oxide support. The reaction results in the elimination of between about 0.5 and 2.0 moles of hydrogen halide per mole of metal halide adsorbed on said support. The reaction temperature will depend upon such variables as the reactivity of the metal halides and its sublimation temperature or boiling point as well as on the nature of the refractory inorganic oxide support. When aluminum chloride and alumina are used, the reaction readily occurs within the range of about 190° C. to about 600° C.

The amount of metal halide which is reacted with the bound surface hydroxyl groups on the support is generally given in terms of the weight percent of the metal on the composite. This amount will vary with the refractory inorganic oxide support used, the relative number of bound surface hydroxyls of the support (which may be related to the particular oxide phase utilized), the specific metal halide employed as well as the particular procedure used to react the metal halide and the bound surface hydroxyl. For example, as a rough rule of thumb for aluminum chloride on alumina, the amount of aluminum chloride reacted expressed as weight percent aluminum in the final catalyst ranges from about 0.1 up to about 2.5% with the level being a function primarily of the number of bound surface hydroxyl groups on the refractory inorganic oxide support.

The feedstocks which can be used in the present invention are mixtures of alkanes and alkenes. The alkanes which may be used contain from 4 to 6 carbon atoms and the branched alkanes are particularly useful in the practice of this invention. Illustrative of the alkanes which can be used in this invention are n-butane, 2-methylpropane, 2-methylbutane, 2,2-dimethylpropane, n-pentane, n-hexane, 2,3-dimethylbutane, 2-methylpentane, 3-methylpentane and 2,2-dimethylbutane.

The alkenes which are used in the practice of this invention contain from 2 to 6 carbon atoms and are ethylene, propylene, the butenes, the pentenes, and the hexenes.

Internal alkenes are favored over terminal alkenes and a particularly desirable alkene is butene-2. The feedstock is a mixture of one or more alkanes and one or more alkenes with the total alkane/alkene ratio being as high as 100:1 and as low as 1:1, although the range between 20:1 through 5:1 is much more usual.

The alkylation reaction is performed as a continuous reaction in the liquid phase. The catalyst generally is present as a fixed bed although this is not a necessary limitation but rather merely represents a convenient reaction mode. The feedstock mixture of alkenes and alkanes is flowed through the catalyst at alkylation conditions which include a temperature of −10° C. to about 100° C. depending upon the particular feedstock used and the nature of the catalysts. Temperatures between about 10° C. and about 50° C. are preferred. Reaction pressures should be sufficient to maintain the reactants in a liquid phase but are not otherwise an important variable. That is, the pressure does not significantly influence the reaction other than maintaining the constituents in a liquid phase. Since the catalyst is employed as a bed, with a liquid phase reactant mixture coming into contact with it, the liquid hourly space velocity of the feedstock is between 0.1 and about 5.0 hr$^{-1}$. Although the feedstock may be contacted with the catalyst bed in either an upflow or a downflow mode, it is somewhat preferable to flow the feedstock in an upflow direction.

The prior basic description may be modified in ways well known to those skilled in the art. For example, one variation is the use of a staged olefin injection, sometimes referred to as interstage olefin injection. In this variation the initial feedstock entering the reaction zone contains a rather high ratio of alkane to alkene. The alkene is rapidly depleted to afford a feedstock very high in alkane content and additional amounts of alkene are injected at various points along the reaction zone. At each point the alkane to alkene ratio remains high because of the rapid depletion of alkene, although the overall alkane to alkene ratio remains between the stated limits of 100:1 to 1:1.

The following examples are presented in illustration of this invention and are not intended as undue limitations on the broad scope of the invention as set out in the appended claims.

EXAMPLE 1

A solution was prepared by combining in a flask 129 g of deionized water, 7.8 g of a potassium hydroxide solution (39.5% KOH) and 4.1 g of EDTA. This solution was heated to boiling and then transferred to a rotary evaporator which was controlled at 70° C. To the evaporator there was added a second solution containing 35.1 g of deionized water and 18.2 g of a solution containing chloroplatinic acid (3.02% Pt). The mixed solution was aged in the evaporator for 45 minutes.

To the aged solution there were added 213.6 g of gamma alumina extrudates. The temperature was raised to 100° C. and the support rolled for 5 hours. The impregnated support was heated to a temperature of 565° C. in dry air. When the temperature was reached, an air stream containing HCl and $Cl_2$ was flowed through the catalyst for 6 hours. Next, the catalyst was reduced by flowing pure hydrogen over the catalyst at a temperature of 562° C. for 2 hours.

One hundred grams of the reduced catalyst was placed in a reactor and treated with hydrogen at 260° C. for 20 minutes. Anhydrous HCl plus hydrogen was now flowed for 45 minutes and then 100 g of $AlCl_3$ in combination with 3 g NaCl was sublimed (upflow) onto the catalyst. Finally, anhydrous HCl was again flowed for 45 minutes.

Analysis of this catalyst showed it contained 0.252 wt. % Pt and 0.98 wt. % K. This catalyst was identified as catalyst A.

EXAMPLE 2

This example presents the preparation of a catalyst according to the prior art. Gamma alumina extrudates were placed in a rotary evaporator and combined with an aqueous solution of chloroplatinic acid and 2.5 wt. % hydrochloric acid. The support/solution mixture was tumbled and heated to 100° C. in order to evaporate the solution. Next, the dried catalyst was calcined at 500° C. in air for 3 hours.

The above impregnation procedure was repeated using a solution of potassium chloride. The resultant calcined catalyst was next reduced with hydrogen and $AlCl_3$ was sublimed thereon as described in Example 1. Analysis of this catalyst showed it contained 0.249 wt. % Pt, and 1.0 wt. % K. This catalyst was identified as catalyst B.

EXAMPLE 3

Catalysts A and B were tested for alkylation activity using a fixed bed reactor operating in an upflow mode using a feedstock of isobutane and 2-butene in a molar ratio of 45. The 2-butene weight hourly space velocity was 0.2 hr$^{-1}$, the reaction temperature was 10° C., and the pressure was 450 psig.

The results of this evaluation are presented in the table below.

TABLE

| Catalyst I. D. | Hours at 100% Conv |
|---|---|
| A | 6 |
| B | 3.5 |

This data shows that the catalyst of this invention can maintain 100% conversion for almost twice as long as a catalyst of the prior art.

We claim as our invention:

1. A process for alkylating a $C_2$–$C_6$ alkene with a $C_4$–$C_6$ alkane to form an alkylate comprising reacting in the liquid phase the alkene with the alkane under alkylation conditions in the presence of a catalyst comprising a particulate refractory inorganic oxide support having dispersed thereon a first component which is at least one Group VIII metal, a second component which is a metal cation and a third component which is the reaction product of a metal halide and bound surface hydroxyl groups of said refractory inorganic oxide; the catalyst characterized in that at least 40 percent of the first component present on the catalyst is located within a band of about 100 to about 300 micrometers beginning at the surface and extending toward the center of the catalyst particle, the second component is uniformly distributed throughout the particle and present in an amount from about 0.1 to about 10 wt. %.

2. The process of claim 1 where the alkylation conditions include a molar ratio of alkane to alkene of about 100:1 to about 1:1, a temperature of about −10° C. to about 100° C. and a pressure sufficient to ensure a liquid phase reaction.

3. The process of claim 1 where the support is selected from the group consisting of alumina, titania, zirconia, chromia, silica, boria, silica-alumina, aluminum phosphate and mixtures thereof.

4. The process of claim 1 where the metal halide is a halide of aluminum, gallium, boron and mixtures thereof.

5. The process of claim 1 where the metal cation is selected from the group consisting of lithium, sodium, potassium, cesium, rubidium, silver, copper(I), beryllium, magnesium, calcium, strontium and barium.

6. The process of claim 1 where the first component is selected from the group consisting of platinum, palladium, nickel, ruthenium, rhodium, osmium, iridium and mixtures thereof.

7. The process of claim 1 where the alkane is isobutane.

8. The process of claim 1 where the alkene is butene.

9. The process of claim 1 where at least 40% of the first component is located in a band of about 100 to about 200 micrometers beginning at the surface of the particle.

10. The process of claim 1 where at least 60% of the first component is located in a band of about 100 to about 200 micrometers beginning at the surface of the particle.

11. The process of claim 9 where at least 60% of the first component is located in a band of about 100 to about 200 micrometers beginning at the surface of the particle.

* * * * *